United States Patent [19]

Kolber et al.

[11] 4,308,231
[45] Dec. 29, 1981

[54] OPTICAL TIMING AND A/D CONVERSION METHOD AND APPARATUS

[75] Inventors: Steven N. Kolber, North Miami Beach, Fla.; Anthony Marino, Doylestown, Pa.; Robert L. Kreiselman, Miami, Fla.

[73] Assignee: Coulter Electronics, Inc., Hialeah, Fla.

[21] Appl. No.: 177,092

[22] Filed: Aug. 11, 1980

[51] Int. Cl.³ .................. G01N 21/27; G01N 1/14
[52] U.S. Cl. .................. 422/64; 250/208; 356/222; 356/246; 356/435; 422/67; 364/497
[58] Field of Search .......... 422/64, 67; 356/246, 356/435, 436, 222; 250/208, 565; 364/497

[56] References Cited

U.S. PATENT DOCUMENTS

| | | | |
|---|---|---|---|
| 3,829,221 | 8/1974 | Ossona de Mendez et al. | 356/201 |
| 4,234,539 | 11/1980 | Ginsberg et al. | 422/67 X |
| 4,234,540 | 11/1980 | Ginsberg et al. | 422/67 X |

FOREIGN PATENT DOCUMENTS 1501833 11/1973 United Kingdom.
1505312 8/1975 United Kingdom.

OTHER PUBLICATIONS

Journal of Automatic Chemistry–Jan. 19, 1979, pp. 72–77.

*Primary Examiner*—Ronald Serwin
*Attorney, Agent, or Firm*—Silverman, Cass & Singer, Ltd.

[57] ABSTRACT

An optical timing and A/D conversion method and apparatus for converting analog signals obtained by movement of a plurality of reaction vessels relative to one or more beams of light from analog to digital signals. The sample signals are obtained each time a reaction vessel passes through a beam of light. The converted digital signals indicate the absorbance of the respective vessels and their contents. Each of the reaction vessels or cuvettes has translucent wall portions providing a radiation path therethrough for the light beams which may be monitored by photometer means in a chemical reaction analyzer. The vessels are repeatedly passed through the light beams of the photometer means as chemical reactions take place therein, the purpose being to monitor the changes in the reaction of the fluids therein by measuring the changes in the absorbance of the vessel and fluids. The sample interval of the analog signal is repeatable for each vessel for each light beam and may be shifted to select the best portion of the analog signal generated as the vessel passes through the particular light beam. The A/D conversion also may eliminate the dark sample or noise error between the light beams and the reaction vessels and may eliminate the variations in the sample signals caused by changes in the rate of relative movement between the beams and vessels and changes in the velocity of the rotating beam.

32 Claims, 13 Drawing Figures

DARK SAMPLE $V_{OFFSET}$ → $V_{OUT} = + V_{OFFSET} \frac{T}{RC}$

HOLD  OPEN → $V_{OUT} = + V_{OFFSET} \frac{T}{RC}$

LIGHT SAMPLE $V_{SIG} + V_{OFFSET}$ → $V_{OUT} = -V_{SIG}\frac{t}{RC} - V_{OFFSET}\frac{t-T}{RC}$ HOLD  OPEN → $V_{OUT} = V_{SIG}\frac{T}{RC}$

OPTICAL TIMING AND A/D CONVERSION METHOD AND APPARATUS

CROSS REFERENCE TO RELATED APPLICATIONS

This invention is related to the subject matter disclosed in the following copending and commonly assigned applications which are incorporated herein by reference:

Apparatus For Monitoring Chemical Reactions and Employing Moving Photometer Means, G. Ginsberg et al, Ser. No. 846,337, filed Oct. 28, 1977, now U.S. Pat. No. 4,234,538.

Sample and Stat Feeding System and Sample Tray, G. Ginsberg et al, Ser. No. 115,924, filed Jan. 28, 1980, now U.S. Pat. No. 4,276,258.

Cuvette Washing Apparatus, B. Hodgins et al, Ser. No. 115,692, filed Jan. 28, 1980.

System and Program for Chemical Reaction Observation with a Moving Photometer, G. Ginsberg et al, Ser. No. 115,734, filed Jan. 28, 1980, now U.S. Pat. No. 4,276,051.

Fluid Transfer Mechanism, V. Drbal et al, Ser. No. 115,691, filed Jan. 28, 1980, now U.S. Pat. No. 4,276,260.

Probe Washer, B. Hodgins, Ser. No. 115,625, filed Jan. 28, 1980.

Variable Stop Syringe, B. Hodgins et al, Ser. No. 115,624, filed Jan. 28, 1980.

BACKGROUND OF THE INVENTION

The invention relates to a system and method for monitoring repeatedly the absorption of electromagnetic radiation by a plurality of specimens occurring during a period of time. More particularly, this invention concerns a system and method in which each of a plurality of samples provides one or more aliquots which are subjected to chemical reaction with different reagents. The absorbance of each aliquot repeatedly is measured during a predetermined reaction time. The term "aliquot" as employed herein is a noun meaning a portion of a sample. The measurement involved herein is accurately ascertaining the absorbance of electromagnetic radiation at a particular wavelength by the fluids in the reaction vessels or cuvettes and converting the signals from an analog to a digital form so that the digital information can be processed, stored and manipulated in a computer.

It would be desirable to make such analysis in a continuous processing mode in which the apparatus can continue to operate so long as there are samples to be tested, the old samples and their tested aliquots being "replaced" by new samples and their aliquots without interruption of the operation of the testing apparatus. Such continuous operation may include one or more photometric measurements on a given aliquot by one or more photometers. It is preferable in receiving the analog absorbance signals each time a reaction vessel passes through a light beam that it be converted into a digital signal.

The continuous analyzers of interest typically supply sample aliquots to the reaction vessels which then are monitored by measuring the absorbance or transmittance by the fluids in the cuvettes of electromagnetic radiation at a particular wavelength or wavelengths. Sample fluids placed in the cuvettes or reaction vessels typically may be body fluids of a specific patient with one or more tests conducted on the sample fluids from each patient related to the patient's health; therefore, it is extremely critical that the signals obtained from the fluids in the cuvettes be both accurate and repeatable. The sample window, the base line and the position of the sample window with respect to the analog signal should be precisely repeatable for each cuvette and each light beam passing through the cuvette.

So far as known, prior art has not taught how to accomplish great accuracy and repeatability in practical devices. For example, optimization of the signals derived from the photometer beams passing through the cuvettes is not disclosed; wow in the rotating photometer carrier is not compensated for, etc.

The invention herein overcomes these and many other disadvantages to provide reliable, accurate and repeatable information on a continuous basis, capable of being processed in a high speed computer.

SUMMARY OF THE INVENTION

The disadvantages of prior art cuvette sampling systems and techniques are overcome in accordance with the present invention by providing an individual window for each cuvette which is precisely repeatable each time that cuvette coincides with and is sampled by a particular photometric light beam. A portion of this analog signal is converted into a digital signal which may be shifted to maximize the results of the integration from the analog signal obtained by the passage of the cuvette through the light beam. Variations in the digital signal due to the dark response or noise error of the system as well as changes in the rate of relative movement are eliminated by the A/D converter.

DESCRIPTION OF THE PREFERRED EMBODIMENTS

Figure 1:
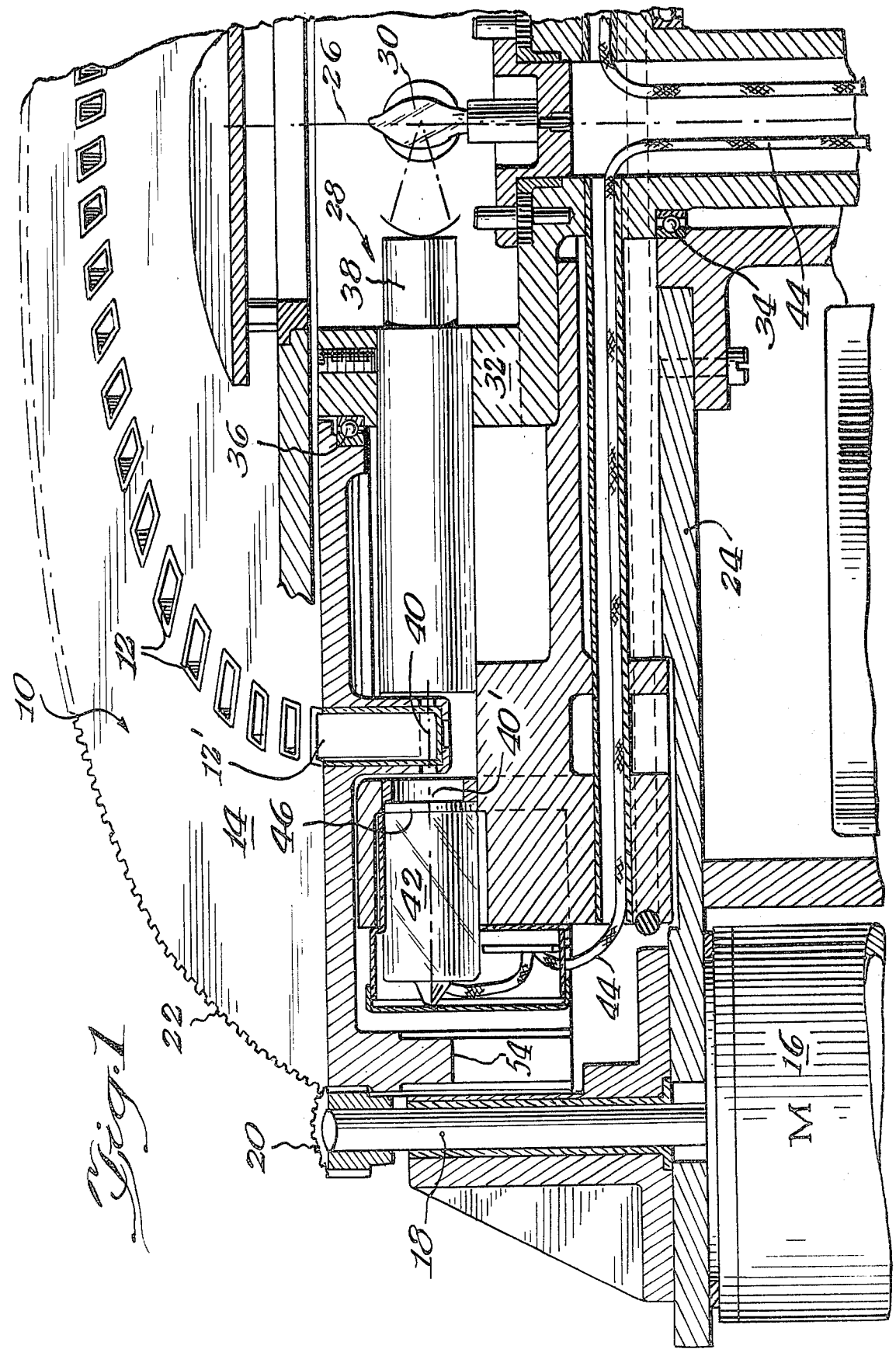
FIG. 1 is a fragmentary median sectional view through the photometric data generating components of a chemical analyzer constructed according to the invention.

Referring now to FIG. 1, a chemical analyzer which may embody the A/D converter constructed in accordance with the invention is designated generally by the reference character 10. The chemical analyzer 10 (partially shown) includes a plurality of cuvettes or reaction vessels 12 which are at least partially translucent and which may be integral with or independently fabricated and installed in a turntable 14 of the analyzer 10. The turntable 14 may be rotated or indexed by a conventional drive mechanism including a motor 16 having a drive shaft 18 including a pinion gear 20 affixed to one end thereof. The pinion gear 20 engages mating teeth 22 on the periphery of the turntable 14. The array of cuvettes 12 will be "indexed" by the motor 16. As used herein the terms "stepped" and "indexed" include but are not limited to discrete movements, since the turntable 14 and hence the array of cuvettes 12 also may be continuously moving slowly without any dwell periods.

The analyzer 10 includes a baseplate 24 to which the motor 16 is mounted and with respect to which the array of cuvettes 12 is rotated around an axis 26. The A/D converter may be utilized with a fixed photometer having a single beam of light or fixed plural photometers having a plurality of light beams through which the array of cuvettes 12 is progressively and sequentially passed or the photometer means may be carried directly on a rotor so that it may be rotated around the axis 26 progressively to pass the light beam or beams through the fixed or indexed array of cuvettes 12.

Indexing the turntable 14 and assuming that the analyzer 10 may be performing various functions as the array of cuvettes 12 is rotated past various stations (such comprising, for example, loading, unloading and cleaning stations) the array of available and sample containing cuvettes 12 essentially is endless; it is preferable that the beam or beams pass at least once and preferably more than once through each cuvette 12 during each step of the turntable 14. One photometer 28 includes a source of radiation or lamp 30 located at the axis 26 of rotation. The photometer means which may be of various constructions are carried by a second rotary member comprising a photometer rotor 32.

The rotor 32 also is driven by drive means (not shown) about the axis 26 on one or a plurality of bearings 34 enabling the rotor to rotate relative to the baseplate 24. The cuvette turntable 14 is mounted on top of the photometer rotor 32 by one or a plurality of bearings 36. The concentric alignment of the photometer rotor 32 and cuvette turntable 32 on the axis 26 provides a precisely repeatable light path through the cuvettes 12 the path being defined by the beam of the lamp 30. Light from the lamp 30 passes into a lens containing optical tube 38 mounted on the rotor 32 having one end proximate to the radiation source or lamp 30 and the other end close to the annular path or pattern traversed by the cuvettes 12.

The tube 38 forms a light beam 40 illustrated as passing through a lower portion of a specific cuvette 12' shown in section in FIG. 1, and through the reaction fluids, if any, in the bottom of the cuvette 12'. The beam of light 40 is partially absorbed by the incident walls of cuvette 12' which provide translucent paths for the light beam and also through the fluids therein, the part of the energy of the light beam 40' not absorbed in passing through the cuvette 12' being received by a photodetector 42. The photodetector 42 generates an analog signal indicative of the intensity of light remaining in the beam 40'. The analog signal is coupled to the A/D converter of the invention by a electrical lead 44.

The A/D converter preferably is mounted upon and rotated with the rotor 32. Once the signals are converted in the A/D converter from analog to a digital form they are transmitted from the rotor 32 to a fixed portion of the analyzer 10 physically separated from the rotor where they can be analyzed, stored, etc. The photodetector 42 may include a filter 46 which will allow radiant energy of only a particular wavelength to be received by the photodetector 42. The rotor 32 may also carry a plurality of photometers similar to 28 each having the optical tube 38 forming a separate beam path directed to respective separate photodetectors 42 carried on the rotor 32. Thus, utilizing a plurality of light beams and photodetectors the cuvettes 12 may be scanned by a plurality of different photometers each generating a signal indicative of the light intensity received at a respectively different wavelength of interest.

As one example of operation, the cuvette turntable 14 may be indexed at a relatively slow rate and may have 120 cuvettes 12 mounted thereon. The turntable 14 is stepped once every six seconds, one full cycle being achieved as a single revolution of the turntable 14 relative to the baseplate 24 every 12 minutes. The rotor 32 and photometer means rotate around the axis 26 at a speed of one revolution every six seconds, being a relatively slow speed of ten revolutions per minute or 120 revolutions of the rotor 32 for each revolution of the cuvette turntable 14. If it is assumed that there are eight radially spaced photometers and that measurements are being made at all times, each cuvette 12 of the cuvette array on the turntable 14 will be photometrically scanned 960 times in a complete cycle relative to the housing or baseplate 24. The amount of data generated and the number of times the cuvettes 12 are scanned require that each time that a cuvette 12 is scanned by one of the light beams 40, the portion of the signal to be analyzed which is received by the photodetector 42 must be repeatable, that is, identical to the signal received on the previous pass of that same light beam or the data will not have the accuracy necessary fully to be utilized in the analyzer 10. Further details of a particular analyzer 10 may be found in the application incorporated herein by reference entitled, Apparatus For Monitoring Chemical Reactions And Employing Moving Photometer Means, Ser. No. 846,337, filed Oct. 28, 1977, now allowed.

Figure 2:
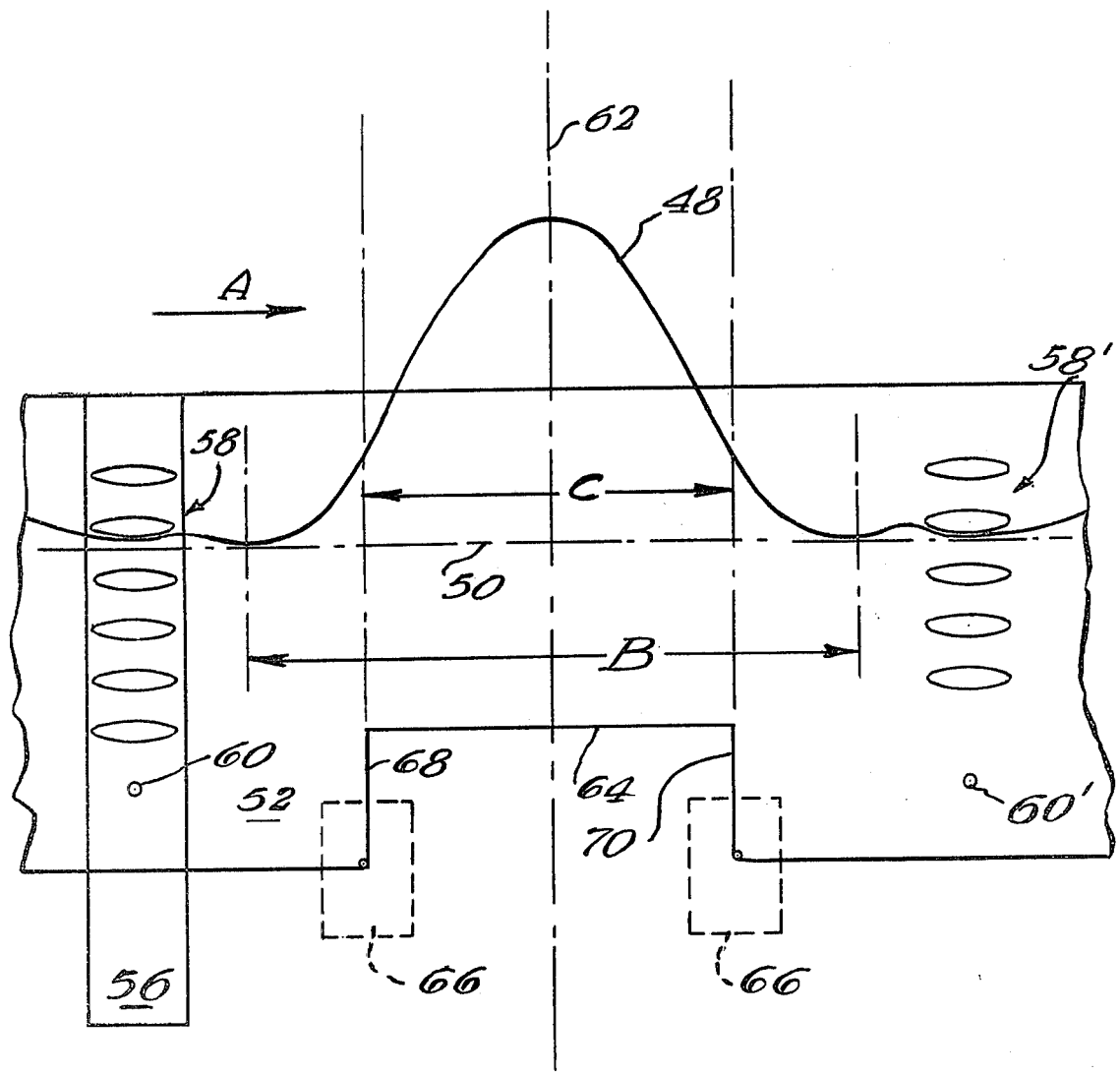
FIG. 2 is a diagrammatic illustration of a timing window with certain signal representations, the window serving to cooperate with the A/D converter of the invention.

Attention is now invited to FIG. 2 which is a combination geometric diagram and electrical signal chart used for the purpose of explaining the sample timing of the A/D converter.

When a cuvette such as 12 containing a sample of some fluid intercepts a passing beam such as 40 some of the radiant energy contained in the beam will impinge on the photodetector 42 associated with that beam (see FIG. 1) and the photodetector will produce a signal (either directly or indirectly) which can be represented as a waveform 48. This waveform 48 is designated $V_{SIG}$ hereafter and identified as a voltage. It will be recalled that the cuvette 12 along with all of the others is set into a solid portion of the turntable 14 so that unless the beam 40 finds an opening in its path no radiant energy from the beam 40 will get to the photodetector. This condition is represented by the base line 50 below the waveform 48 and comprises the theoretical zero or dark condition.

Assume that the rotor 32 is moving relative to the cuvette turntable 14 and that at the time of the diagram of FIG. 2, the cuvette turntable 14 has stopped in its stepping action. The beam 40 from the photometer 28 of whatever photometer means are carried on the rotor 32 will pass the position of the cuvette 12 in a direction which is indicated by the arrow A. As it passes, assuming that its velocity will be constant (which is a preferred form of rotation of the rotor 32), the waveform 48 which is illustrated will be generated in the photometer circuit. This is an analog signal and is shown as an idealized smooth signal but may vary from that shown depending upon light beam alignment with the cuvette 12, beam diameter, noise, the speed of the rotor 32, etc.

The amplitude of the analog signal $V_{SIG}$ will increase from the base line 50 to the peak of the curve when the beam is in its most favorable alignment with the cuvette 12 and the photodetector 42 and then decreases back again to the base line 50 as the beam passes into the next imperforate wall portion between cuvettes. Thus the waveform 48 for a particular cuvette may have a total duration as indicated at B, assuming the horizontal axis is time. In optical and electrical instruments it is not preferable to sample the total waveform 48 encompassed by the time B and hence it would be preferable to select a small portion such as defined by C to sample the most reliable center portion of the sample signal $V_{SIG}$. This portion may be termed a "window". The peak amplitude of $V_{SIG}$ will vary as the absorbance of the cuvette varies and will also be dependent on the wavelength of the radiant energy of the beam 40.

The sample signal illustrated by waveform 48 will be produced in the photodetector whether the cuvette 14 is in a dwell (stopped position) or whether the photometer 28 is moving faster than the cuvette turntable 14. Relative movement is produced in each case. Each of the cuvettes 12 in the cuvette array has a specific position numbered 1, 2, 3, etc. through the total number of cuvettes in the cuvette array. On this account it also is essential that the analyzer 10 have the capability of determining which of the cuvettes 12 is responsible for the sample signal or waveform 48 which is produced by a given photodetector. Further, a sample signal will be obtained substantially simultaneously for each photometer of the photometer means carried by the rotor 32 assuming there is a plurality. Preferably, each of these photometers will have a light beam derived from a light tube such as 38 illustrated in FIG. 1. For equiangular radial spacing on the rotor 32, each photodetector will be generating a waveform similar to 48 for a different cuvette at the same instant of time.

One method of obtaining information describing the correct cuvette position is to provide a code skirt or band 52 carried by the cuvette turntable 14 depending from the outer periphery of the turntable 14 radially inward of the shaft 18 at 54 in FIG. 1. The rotor 32 may carry an optical reader 56 (FIG. 2) on its outer periphery with the code skirt 52 passing between the arms of the optical reader 56 in a conventional manner. The reader 56 will carry a series of photodiodes which will generate an identification signal produced by the light pattern passing therebetween from a code array 58 formed in the band 52 for each cuvette position. The arrays 58 and the reader 56 identify each cuvette position to enable the analyzer 10 to match the proper sample signal with its respective cuvette 12. Each code array 58 will include a strobe hole 60 to ensure that the physical alignment of the reader 56 with the array 58 is such that the correct identification reading will be made by the reader 56 each time it senses one of the arrays 58. The array 58' for the next cuvette position will have a different set of optical holes to form an optical code different from that of the array 58 to identify its respective cuvette position.

Not only must the proper cuvette 12 be matched with the proper sample signal or waveform 48, but the sample signal waveform 48 must be positionally repeatable each time the individual cuvette is ready by the same photometer 28. The center line of the waveform 48 is indicated at 62. It is not essential that the sample portion C be perfectly centered on the center line 62; however, whether it is shifted to the right or left it is essential that the sample portion have the identical alignment each time the individual cuvette is sampled by the same photometer. Each of the photometers may include a reader similar to the reader 56, or their respective cuvette positions may be empirically obtained merely from their positioning relative to the reader 56.

To obtain the same sampling portion C a timing window must be generated for each one of the photometer means for each cuvette position. One way of providing the timing window is to form a structural window 64 for each position which is a notch cut into the bottom periphery of the code band 52. In such case the A/D converter will sample the portion C by means of a second reader shown in two positions, in phantom lines at 66, which will trigger the start of the sampling period C when it reads the presence of the window 64 and which will terminate the sampling period C when it reads the trailing edge 70 of the window or notch. Alternatively, the timing window may be generated electronically as will be discussed hereinafter with respect to FIGS. 4 and 4A.

The reader 66 will also be carried by the photometer rotor 32 and each photometer may include a separate reader similar to the reader 66 or may generate respective timing windows from a pulse derived from the optical reader 66 and the known position from the reader 66. In utilizing the physical window 64 the edges 68 and 70 must be very accurate; however, since the physical window may be aligned for one photometer and its light beam, it may not be optimally aligned with the axis 62 of the sample waveforms 48 generated by other photometers as they pass the same or other cuvette positions.

Figure 3:
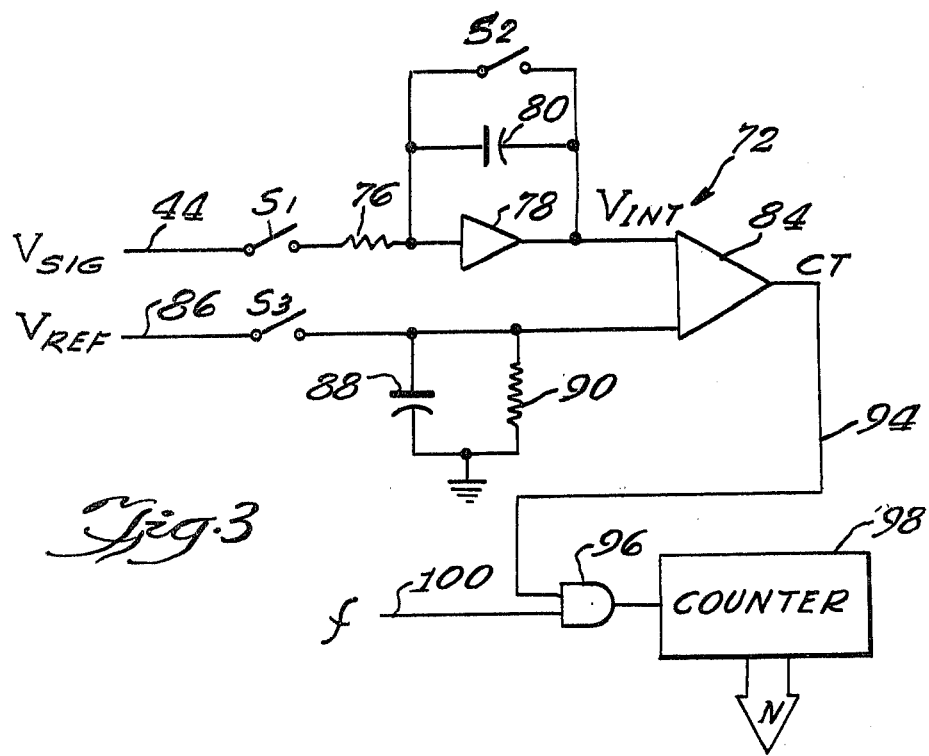
FIG. 3 is a schematic combined block and circuit diagram of the A/D converter.
Figure 3A:
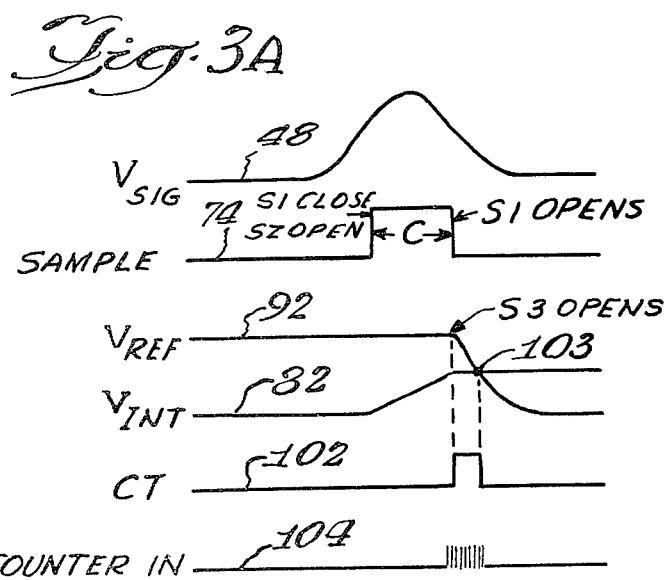
FIG. 3A is a chart illustrating the timing of the operations of the circuit of FIG. 3.

Referring to FIGS. 3 and 3A, the sample waveform 48 is converted from an analog to a digital signal in an A/D converter 72 prior to being coupled from the rotor 32 to the control and analyzing section of the analyzer 10. Converting the signal peak or intensity from analog to digital form eliminates the inherent difficulties of accurately transmitting an analog signal from the rotating rotor 32 to a fixed receiver on the frame 24. $V_{SIG}$ as illustrated by the waveform 48 in FIGS. 2 and 3A is applied on the line 44 (FIG. 1) to a switch S1. The switch S1 is closed and opened by signals derived from the window 64 illustrated in FIG. 2 or electronically to form the sampling period or timing window C as illustrated by the waveform 74 in FIG. 3A.

All signals illustrated in FIG. 3A are on the same horizontal time axis.

The sample signal $V_{SIG}$ is coupled through the closed switch S1 through a load resistor 76 to an integrator 78. The integrator 78 includes a capacitor 80 which is maintained in a discharged condition by a switch S2 connected in parallel with the capacitor 80 when the sample signal is not present. When the switch S1 is closed to couple the sample signal $V_{SIG}$ to the integrator 78, the switch S2 is opened to permit the normal integrating function to occur. The integrator 78 generates an output signal $V_{INT}$ illustrated by the waveform 82 in FIG. 3A. The integrator output signal $V_{INT}$ is coupled to one input of a comparator 84.

The second input of the comparator 84 is controlled by an RC network which is charged by a reference voltage or signal $V_{REF}$ applied to a line 86. The reference signal is normally applied to the RC network formed by a capacitor 88 and a resistor 90 through a switch S3. When the sampling period C terminates the switch S3 is opened allowing the capacitor 88 to discharge as illustrated by the waveform 92. When the sampling period C is terminated the switch S2 is still open and the switch S1 is opened so that the magnitude of the signal $V_{INT}$ applied to the first input of the comparator 84 is maintained at a fixed value. The comparator 84 generates a square wave as a counting interval CT on a line 94 which is coupled through an AND gate 96 to a counter 98. The second input of the AND gate 96 is a high frequency signal f applied on a line 100. The comparator counting interval CT is illustrated by a waveform 102.

The counter 98 counts the number of pulses from the line 100 which are included within the time period defined by the comparator counting interval 102 which terminates when the second input of the comparator 84 is equal to the first input as shown by waveforms 82 and 92. The point where this occurs is at 103. The counter 98 input carries a number of pulses from the line 100 at the frequency f which have been counted during the interval CT (waveform 104) and provides its output as a digital number N. The number N is the digital conversion of the analog signal $V_{SIG}$ for the sample period C determined by the values of the frequency f, the capacitor 88 and the resistor 90. The digital signal N may then be coupled to the analyzing and control circuits of the analyzer 10.

The timing diagram in FIG. 3A illustrates that a time shift of the sampling period C with respect to $V_{SIG}$ (waveform 48) would result in a different digital output even though the signal 48 was exactly the same. Accordingly, it is essential that the window remain the same so that the changes in the waveform 48 from sampling period to sampling period for any particular cuvette may be obtained accurately.

For the circuit shown in FIG. 3 the digital output N is a linear representation of absorbance (ABS) as shown by the following derivation:

---
PHOTOMETER OUTPUT

DEFINITION: $I_\phi$ = % Transmission $$\% \text{ Trans} = 10^{(2-ABS)}$$

SAMPLING PROCESS:
$$V_1 = I_\phi \cdot \frac{T_1}{C_1} \quad (T_1 = \text{sample interval} = C)$$

$$V_1 = V_{SIG} = K \cdot \% \text{ Trans} \left( K = \frac{T_1}{C_1} \right)$$

CONVERSION PROCESS:
$$V_2 = V_{REF} \cdot e^{-\frac{t}{RC}}$$

when $V_1 = V_2$ (t = N/f)

$$K \cdot \% \text{ Trans} = V_{REF} \cdot e^{-\frac{N}{fRC}}$$

---
PHOTOMETER OUTPUT -continued substituting:
$$K \cdot 10^{(2-ABS)} = V_{REF} \cdot e^{-\frac{N}{fRC}}$$

$$\ln K + (2-ABS) \cdot \ln 10 = \ln V_{REF} - \frac{N}{fRC}$$

which yields:
$$ABS = \frac{N}{fRC \ln 10} + 2 - \frac{\ln \frac{V_{REF}}{K}}{\ln 10}$$

This is a straight line:

$$\text{Slope} = \frac{1}{fRC \ln 10}$$

$$\text{INTERCEPT} = 2 - \frac{\ln \frac{V_{REF}}{K}}{\ln 10}$$

(f = frequency f on line 100, R = resistor 90, C = capacitor 88)

---

Figure 4:
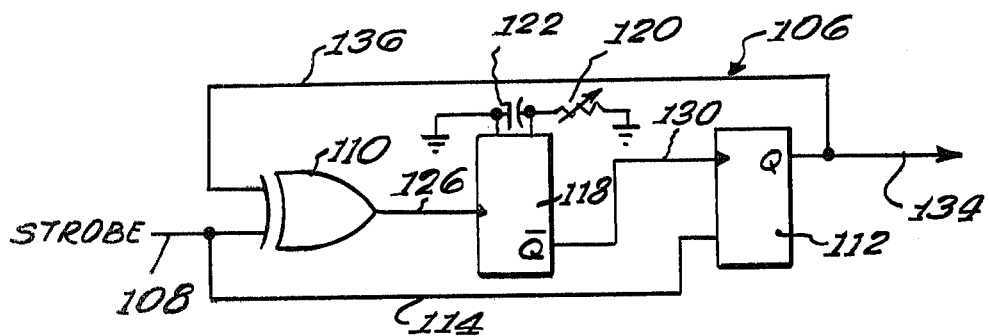
FIG. 4 is a block diagram of the window alignment circuit of the A/D converter.

As mentioned above it is feasible to generate a synthetic timing window electronically instead of utilizing the provision of a physical notch cut into the bottom edge of the code band 52. The generation of the electronic sampling window through the utilization of the circuit 106 will now be explained in connection with FIGS. 4 and 4A. FIG. 4 is the circuit which is used and FIG. 4A is a chart of the signals or waveforms which are produced, all being aligned vertically on a common horizontal time axis.

Figure 4A:
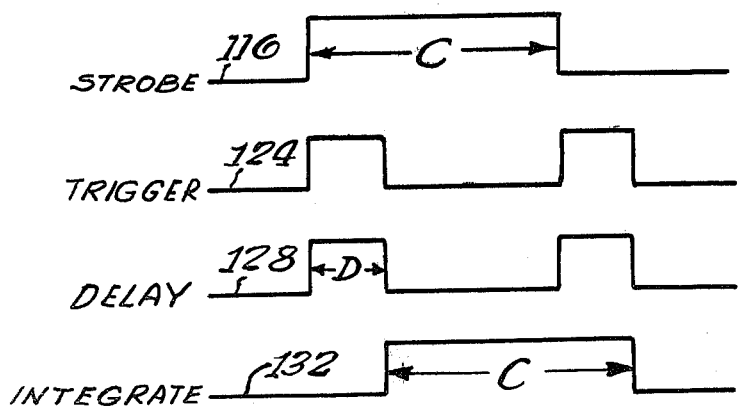
FIG. 4A is a chart illustrating the timing of the operation of the circuit of FIG. 4.

The generation commences by means of a strobe signal identified by the designation STROBE in FIG. 4A derived from the reader 56 and the strobe hole 60 which can be seen in FIG. 2. The signal is applied by way of the line 108 in the circuit 106 of FIG. 4 to an exclusive OR gate 110 and to a delay flip-flop 112 by way of the line 114 that is an extension of the line 108.

The strobe signal initiated by the strobe hole 60 and which is illustrated in FIG. 4A as the wave form 116 has a duration sufficient to generate the proper size window C. The strobe signal 116 could also have been generated by the notch 64 which could be considered a physical strobe window (see FIG. 2).

The output of the OR gate 110 appears on the line 126 which is connected to a delay one shot device 118. The leading edge of the STROBE signal 116 is applied to the device 118 and triggers this device so that a square wave output is produced at the line 130. This is shown in FIG. 4A by the wave shape 124. The trailing edge of the signal 116 also serves to produce a second square wave on the line 130 and this is also shown on the waveform 124.

The duration of the square wave trigger illustrated on the left of the wave shape 124 in FIG. 4A is controlled by the RC combination consisting of the resistor 120 and the capacitor 122. The resistor 120 is variable to enable an adjustment of the duration of the square wave which becomes the delay provided by the delay one shot device 118. The output signal from the delay one shot device 118 appears at the line 130 and is the same as the duration of the signal illustrated as the waveform 124, this delay being designated "D" in the waveform 128. The line 130 connects with the flip-flop 112 as one of the inputs to that flip-flop. It is the delay "D" which can be adjusted by the variable resistor 120.

The trailing edge of the DELAY pulse of wave form 128 sets the flip-flop, generating the leading edge of the integrate signal (INTEGRATE) which is illutrated as the waveform 132 of FIG. 4A. The INTEGRATE signal 132 appears as the output of the flip-flop 112 on the line 134. This line may comprise the control of the switch S1 (see FIG. 4). The trailing edge of the INTEGRATE signal 132 is generated by the second square wave trigger signal on the waveform 124 which provides the same delay "D" as the DELAY signal on the line 130, the trailing edge of the delay signal resetting the flip-flop 112. When the flip-flop 112 is set, the INTEGRATE signal is also fed back on the line 136 through the OR gate 110 on the line 126 to cause the OR gate 110 to invert the STROBE signal on the line 126. The one shot 118 is triggered again on the trailing edge of the waveform 116 as previously mentioned to provide the second positive transition of the trigger signal 124.

Utilizing a circuit 106 with each photometer and its A/D converter 72 results in each photometer having its own INTEGRATE pulse from the system STROBE exactly reproducing the strobe width, but allowing the INTEGRATE signal to be delayed or shifted to align with respective peaks for the individual sample signal peaks. Thus only a single reader 56 is utilized and the individual photometer window alignments may be shifted using the alignment circuit 106.

To achieve a very accurate digital signal N, especially at high absorbance levels (i.e. low magnitude output signals from the photodetector 42) errors due to the electronic and physical alignments of the light path should be eliminated. To eliminate the noise and alignment errors in the system and to achieve the base line 50 an auto-zero circuit 138 may be utilized, as such circuit being illustrated in FIG. 5.

Figure 5:
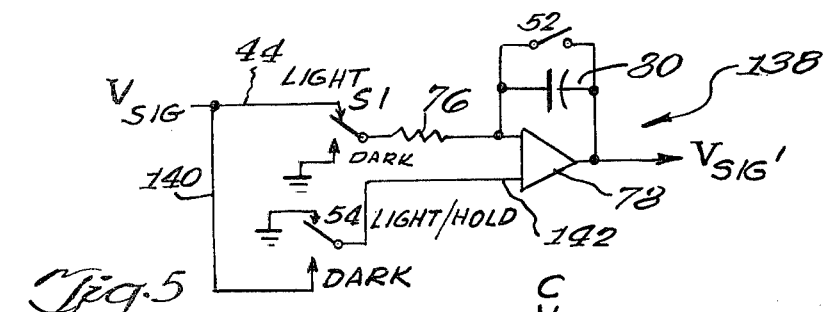
FIG. 5 is a circuit diagram of a noise elimination circuit of the A/D converter.

Referring to FIG. 5 the sample signal $V_{SIG}$ (waveform 48) is coupled on a first line 44 to the switch S1, through the resistor 76 and then to one input of the integrator 78 as previously described with respect to FIG. 3. The sample signal also is coupled on a line 140 to a switch S4 and then to a second input of the integrator 78 on a line 142.

Figure 5A:
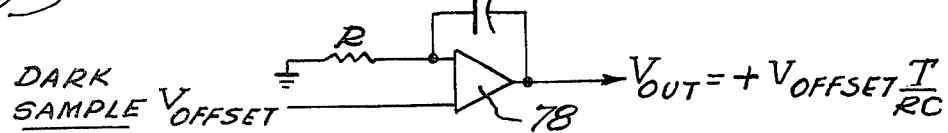
FIGS. 5A–5D are schematic diagrams of the circuit of FIG. 5 utilized in explaining the operation thereof.
Figure 5B:
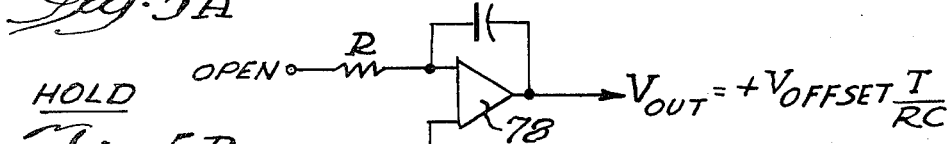
Figure 5C:
Figure 5D:
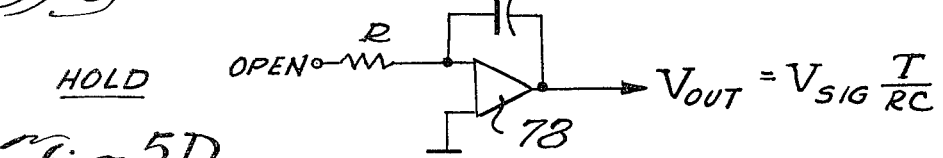
Figure 5E:
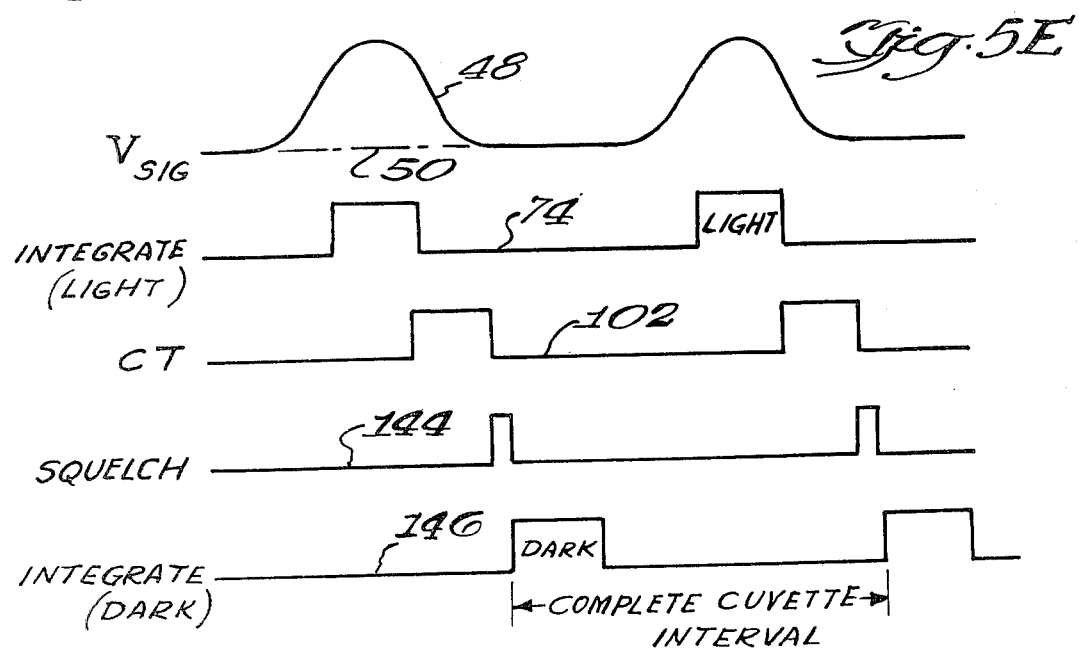
FIG. 5E is a chart illustrating the timing of the operation of the circuit of FIG. 5.

Referring to FIG. 5E, the signal $V_{SIG}$ is integrated for the sample period indicated shown by the waveform 74 and is then converted through the A/D interval as shown by the waveform 102. Following the digital conversion the integrator squelch is applied by closing switch S2 as shown by waveform 144. Following the integrator squelch the dark signal is integrated to take a dark sample as shown by waveform 146.

In operation the dark sample is first generated as shown by FIG. 5A. A voltage called $V_{OFFSET}$, which is the voltage resulting from any electronic or optical system errors is present between cuvettes and may vary in magnitude between cuvettes. $V_{OFFSET}$ would move the actual voltage base line from the desired base line 50 to some value representative of the noise or error. To eliminate the error the $V_{OFFSET}$ first is integrated with the integrator 78 operating in reversed polarity mode. $V_{OFFSET}$ is coupled by switch S4 to the integrator 78 with switch S1 being grounded as indicated in FIG. 5A. This results in a signal:

$$V_{OUT} = V_{OFFSET}(T/RC)$$

In this equation T is equal to the integration interval (waveform 102), R is equal to the charging resistor 76 and C is equal to the value of the capacitor 80.

Following the dark sample period illustrated in FIG. 5A, switch S4 is switched to ground and switch S1 is opened (i.e. contacting neither ground nor input line 44). The hold circuit is shown in FIG. 5B with signal $V_{OUT}$ maintained as:

$$V_{OUT} = +V_{OFFSET}(T/RC)$$

This value is held until the next light sample period (waveform 74) which is shown in FIG. 5C where the input $V_{SIG} + V_{OFFSET}$ is coupled by switch S1 to the integrator 78, enabling integration in the normal polarity made. During the integration interval, the output of the integrator 78 is $$V_{OUT} = -V_{SIG}\frac{t}{RC} - V_{OFFSET}\frac{t-T}{RC},$$

where t indicates the length of time the integration is in process. When t+T the integration ends, and $$V_{OUT} = -V_{SIG}(T/RC).$$

Thus, the dark sample voltage is cancelled and the true reading of $V_{SIG}$ is integrated and held as shown in FIG. 5D. The offset value is cancelled out of the integrated value. Whatever noise or light interference exists in the dark sampling period is effectively cancelled out when the light sample signal is integrated with the offset value.

Figure 6:
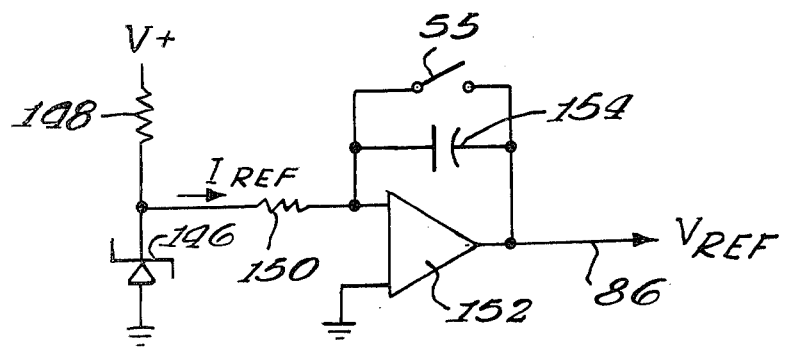
FIG. 6 is a diagram of a circuit utilized to eliminate errors in the A/D converter due to changes in relative movement between components of the system.

To eliminate any changes in rate of movement (WOW) from the digital conversion a WOW circuit 145 may be coupled to line 86 to change signal $V_{REF}$. The WOW circuit 145 eliminates errors due to fluctuations in the relative motion between the turntable 14 and rotor 32. The signal $V_{REF}$ as originally chosen is picked to be a value (FIG. 3A) which is greater than the largest value of the integrate signal $V_{INT}$ shown by waveforms 82 and 92. To adjust the output N for WOW variations, the $V_{REF}$ circuit may be modified by having the integrate pulse width vary inversely with rotational speed. Thus when the rotor 32 speed increases the sample window C will decrease and when the rotational speed decreases the sample window C will be increased by proportional amounts. The WOW circuit 145 is illustrated in FIG. 6.

Examining the intercept term previously derived, if the constant K is replaced by its equivalent value T1/C1, the intercept term is dependent upon T1 and hence the output N also is dependent upon T1 (the integration interval). If however $V_{REF}$ is generated by:

$$V_{REF} = \frac{I_{REF} \cdot T_1}{C_{REF}},$$

Then the intercept term will equal:

$$\text{INTERCEPT} = 2 - \left[ \frac{\ln \frac{I_{REF} \cdot T_1}{C_{REF} \cdot \frac{T_1}{C_1}}}{\ln 10} \right]$$

-continued
$$\text{INTERCEPT} = 2 - \frac{\ln \frac{I_{REF} \cdot C_1}{C_{REF}}}{\ln 10}$$

The intercept term now is independent of the sampling period $T_1$ (C of waveform 74). The WOW circuit 145 includes a zener diode 146 and a load resistor 148 coupled to a reference source voltage V+. This divider generates a current $I_{REF}$ through a resistor 150 to one input of an integrator 152. The integrator 152 includes a capacitor $C_{REF}$ 154 and a switch S5 which is operated during the sampling period C (equivalent to the sampling time $T_1$) opposite of switch S1. When S1 is closed C5 is opened and when S1 is opened S5 is closed. This generates the voltage $V_{REF}$ which is directly proportional to the sampling window C.

Many modifications and variations of the present invention are possible in light of the above teachings. The means for relative motion between the cuvettes and the light beams are not critical to the A/D converter and timing of the invention. The paths of the cuvettes may be parallel and not rotational. The light beam generating also is not critical and could be performed by light guide means and/or mirrors. It is, therefore, to be understood that within the scope of the appended claims, the invention may be practiced otherwise than as specifically described.

What is claimed and desired to be secured by Letters Patent of the United States is:

1. Apparatus of the type in which a reaction effect in a cuvette is measured by passing a beam of radiant energy through said cuvette and detecting the degree of absorbance of the radiant energy as a measure of the said reaction effect,
  in which structure is provided for optimizing the period of time during which the measurement is taking place relative to the alignment of the beam and cuvette to obtain data concerning said measurement, said structure comprising:
  A. a carrier having a plurality of at least partially transparent cuvettes mounted thereon and each cuvette adapted to have an individual reaction sample therein to be subjected to said beam,
  B. means for generating said beam and means responsive to the unabsorbed radiant energy of said beam after it has passed through a cuvette and reaction sample therein, if any, to produce a reaction effect signal,
  C. means for moving the carrier and beam generating means relative to one another whereby to cause the beam to scan the cuvettes seriatim for producing a separate reaction effect signal each time said beam passes a cuvette, the duration of each reaction effect signal being related to the time required for the beam to scan the particular cuvette and having an amplitude related to the beam absorbance in said particular cuvette,
  D. identification means associated with said carrier for producing signals identifying the respective cuvettes,
  E. means for photoresponsively triggering the sampling of the reaction effect signal only when the beam and the center of each cuvette are in coincidence and for a predetermined time before and after coincidence, and
  F. means for converting each reaction effect signal sample into respective data indicative of the absorbance of the reaction sample in said cuvette and the portions of said cuvette through which said beam has passed individual to the identifying signal of said cuvette.

2. The structure as claimed in claim 1 in which said means for sampling said reaction effect signal produces an integration window.

3. The structure as claimed in claim 2 in which the carrier and beam generating means move relative to one another in a manner which causes the beam to scan the cuvettes a plurality of times during which said data are generated.

4. The structure as claimed in claim 2 in which the carrier comprises a turntable mounting the cuvettes and the beam generating means comprise at least one photometer mounted on a rotor coaxial with the turntable, the speed of rotation of the rotor being substantially greater than that of the turntable so that the beam of the photometer scans the cuvettes a plurality of times during each revolution of the turntable, generating a different reaction effect signal for each cuvette each time that said cuvette is scanned.

5. The structure as claimed in claim 4 in which there is a plurality of photometers mounted radially on the rotor and each producing a different beam of radiant energy and each scanning the cuvettes a plurality of times for each rotation of the turntable and generating said data for each cuvette and each beam each time a cuvette is scanned.

6. The structure as claimed in claim 3 in which means are provided for generating the integrating window at the same location relative to any cuvette irrespective of the number of times the beam has scanned the same.

7. The structure as claimed in claim 1 in which said means for sampling said reaction effect signal comprises a physical window formed on said carrier and angularly aligned respectively with each cuvette.

8. The structure as claimed in claim 2 in which means are provided for generating an offset signal during the time period which occurs between respective coincidences of cuvettes and said beams and means are provided for subtracting said offset signal from the reaction effect signal of the cuvette when said latter cuvette is coincident with said beam.

9. The structure as claimed in claim 2 in which means are provided for maintaining the data conversion relationship for each said reaction effect signal irrespective of variation of the rate of relative movement between the carrier and beam generating means.

10. The structure as claimed in claim 3 in which means are provided for maintaining the data conversion relationship for each said reaction effect signal irrespective of variation of the rate of relative movement between the carrier and beam generating means.

11. The structure as claimed in claim 4 in which means are provided for maintaining the data conversion relationship for each said reaction effect signal irrespective of variation of the rate of relative movement between the carrier and beam generating means.

12. The structure as claimed in claim 1 in which means are provided for converting the generated data into digital form, said means being also mounted on the carrier.

13. The structure as claimed in claim 2 in which said means for sampling said reaction effect signal comprises a separate strobe means individual to each cuvette, and circuitry associated with said strobe means for electronically generating said integration window for each cuvette.

14. The structure as claimed in claim 5 in which means are provided for generating an offset sample signal during the time periods between respective coincidence of said cuvettes and said beams and means are provided for subtracting the offset sample signal individual to each cuvette from the reaction effect signal produced by said last-mentioned cuvette.

15. The structure as claimed in claim 5 in which means are provided for maintaining the data conversion relationship for each said reaction effect signal irrespective of variation of the rate of relative movement between the carrier and beam generating means.

16. The structure as claimed in claim 2 in which means are provided for electronically shifting the windows to achieve proper alignment.

17. A method of obtaining data relating to the absorbance of a beam of radiant energy of a predetermined wavelength through a plurality of at least partially transparent reaction vessels, each vessel containing a reaction sample of an individual character relative to the other reaction samples in the other reaction vessels, the beam of radiant energy having an optical axis, the beam being passed relative to all of the vessels to scan the same seriatim, the amount of energy remaining in the beam after passing through each cuvette being measured and adapted to be utilized to derive the said absorbance data, the method comprising:
A. repeatedly passing said reaction vessels through said optical axis in a plurality of cycles,
B. generating a train of sample signals by said passage, each signal being related to the absorbance of a respective vessel and its contents if any, the sample signals each being generated when the sample vessel individual thereto is substantially coincident with said optical axis,
C. moving a plurality of window generating means for photoresponsive sampling from said signals, equal in number to said sample vessels and each being individual to a vessel, in synchronism with the vessels relative to said optical axis,
D. generating an integrating signal defined by said at least one window generating means as it moves relative to said optical axis,
E. gating each sample signal with the integrating signal individual thereto, and
F. generating data from the gated sample signals.

18. The method as claimed in claim 17 including:
identifying each sample vessel and the sample signal related thereto as each said sample vessel passes through said optical axis.

19. The method as claimed in claim 17 including:
providing a structural window aligned with each vessel; and
generating said integration signal by sensing said structural window of each vessel as said optical axis and vessel coincide.

20. The method as claimed in claim 17 including:
generating an offset sample signal during the time period between coincidence of said vessels and said optical axis; and
subtracting said offset sample signal from each sample signal generated when said optical axis and vessels coincide.

21. The method as claimed in claim 17 including:
effectively maintaining said integrating signal substantially the same irrespective of changes in the rate of relative movement between said vessels and optical axis.

22. The method as claimed in claim 17 including:
converting said generated data into digital form.

23. The method as claimed in claim 17 including:
providing strobe means associated with each vessel and generating said window electronically by sensing said strobe means.

24. The method as claimed in claim 23 including:
said photometer means having at least two light beams, each beam having an optical axis coinciding with different ones of said vessels during said relative movement and each generating a separate sample signal as said optical axes and vessels coincide.

25. The method as claimed in claim 24 including:
generating an offset sample signal during the time period between coincidence of said vessels and said optical axes; and
subtracting said offset sample signal from said sample signal generated when said optical axes and vessels coincide.

26. The method as claimed in claim 24 including:
effectively maintaining said integration signal substantially constant irrespective of changes in the rate of relative movement between said vessels and optical axes.

27. The method as claimed in claim 24 including:
each of said vessels and beams having a predetermined spacing from one another;
generating said windows by sensing said strobe means for each vessel scanned by one of said light beam; and
electronically generating said window for each of said other beams and their respective vessels from the predetermined spacing of the other beams from said one light beam.

28. The method as claimed in claim 27 including:
individually shifting said windows to align the windows of the other beams with their respective vessels from said one light beam.

29. The apparatus as claimed in claim 2 in which means are provided for compensating for changes in the duration of the integration window by reason of variation in the speed of the beam generating means relative to the carrier, the apparatus including a comparator for generating said window, means coupling the reaction effect signal to one side of the comparator and a reference signal to the other side of the comparator, the compensating means comprising a circuit responsive to the said speed variation to vary the reference signal.

30. The structure as claimed in claim 2 further including means for varying the size of said integration window inversely with changes in the rate of relative movement between said vessels and the beam generating means.

31. The structure as claimed in claim 7, wherein said physical window generates an integration window.

32. The apparatus as claimed in claim 13 wherein each said strobe means comprises an aperture formed in said carrier for transmission of said strobe trigger therethrough, and separated from said alignment with any of said cuvettes.

* * * * *